United States Patent [19]

Karol

[11] Patent Number: 4,758,361

[45] Date of Patent: Jul. 19, 1988

[54] LUBRICATING OIL OF IMPROVED ANTI-FRICTION PROPERTIES CONTAINING HYDROXYHYDROCARBYL MERCAPTO ESTER OF A $C_1$–$C_{40}$ FATTY ACID SUCH AS THAT DERIVED FROM COCONUT OIL

[75] Inventor: Thomas J. Karol, Wappingers Falls, N.Y.

[73] Assignee: Texaco Inc., White Plains, N.Y.

[21] Appl. No.: 611,661

[22] Filed: May 18, 1984

[51] Int. Cl.[4] .......................................... C10M 105/32
[52] U.S. Cl. ................................ 252/48.6; 252/48.2; 558/252
[58] Field of Search ........................ 252/48.2, 48.6; 260/455 R

[56] References Cited

U.S. PATENT DOCUMENTS

| | | | |
|---|---|---|---|
| 2,201,535 | 5/1940 | Harris | 260/400 |
| 2,520,748 | 8/1950 | Vaughan et al. | 252/48.6 |
| 2,540,570 | 2/1951 | Cyphers | 252/48.6 |
| 2,556,134 | 6/1951 | Croxall et al. | 260/455 R |
| 2,601,063 | 6/1952 | Smith et al. | 252/48.6 |
| 2,603,604 | 7/1952 | Ballard et al. | 252/48.6 |
| 2,624,752 | 1/1953 | Morris | 252/48.6 |
| 2,628,974 | 2/1953 | Sanderson | 252/48.6 |
| 3,766,069 | 10/1973 | Hotten | 252/48.6 |
| 4,000,173 | 12/1976 | Jager et al. | 260/455 R |

OTHER PUBLICATIONS

CA:83:178346u, Kurooka, vol. 83, 1975.

Primary Examiner—William R. Dixon, Jr.
Assistant Examiner—Margaret B. Medley
Attorney, Agent, or Firm—Robert A. Kulason; James J. O'Loughlin; Carl G. Seutter

[57] ABSTRACT

Lubricating oil, containing a beta-hydroxethyl mercapto ester of a fatty acid derived from coconut oil, is characterized by improvement in anti-wear and anti-friction properties.

11 Claims, No Drawings

LUBRICATING OIL OF IMPROVED ANTI-FRICTION PROPERTIES CONTAINING HYDROXYHYDROCARBYL MERCAPTO ESTER OF A $C_1$–$C_{40}$ FATTY ACID SUCH AS THAT DERIVED FROM COCONUT OIL

FIELD OF THE INVENTION

This invention relates to lubricating oil. More particularly it relates to lubricating compositions containing an additive which imparts improvement in anti-wear and anti-friction properties.

BACKGROUND OF THE INVENTION

As is well known to those skilled in the art, lubricating compositions contain a wide range of additives including those which possess anti-wear properties, anti-friction properties, anti-oxidant properties, etc. Those skilled in the art continue to seek additives which may effect improvement in these properties without detrimental effect on other properties—and preferably additives of lower cost.

It is an object of this invention to provide a lubricating composition containing a novel additive. Other objects will be apparent to those skilled in the art.

STATEMENT OF THE INVENTION

In accordance with certain of its aspects, this invention is directed to a lubricating composition comprising (i) a major portion of a lubricating oil; and (ii) a minor effective portion of, as additive, a hydroxyhydrocarbyl mercapto ester of a $C_1$–$C_{40}$ fatty acid.

DESCRIPTION OF THE INVENTION

The composition which may be employed in practice of the process of this invention may be a hydroxyhydrocarbyl mercapto ester of a $C_1$–$C_{40}$ fatty acid.

The fatty acid moiety may be characterized by the formula RCOO—.

Typical fatty acids may include:

TABLE

Caprylic
Capric
Lauric
Myristic
Palmitic
Stearic
Oleic
Linoleic etc.

In the above compound, R may be a hydrocarbon group selected from the group consisting of alkyl, aralkyl, cycloalkyl, aryl, alkaryl, alkenyl, and alkynyl including such radicals when inertly substituted. When R is alkyl, it may typically be methyl, ethyl, n-propyl, iso-propyl, n-butyl, i-butyl, sec-butyl, amyl, octyl, decyl, octadecyl, etc. When R is aralkyl, it may typically be benzyl, beta-phenylethyl, etc. When R is cycloalkyl, it may typically be cyclohexyl, cycloheptyl, cyclooctyl, 2-methylcycloheptyl, 3-butylcyclohexyl, 3-methylcyclohexyl, etc. When R is aryl, it may typically be phenyl, naphthyl, etc. When R is alkaryl, it may typically be tolyl, xylyl, etc. When R is alkenyl, it may typically be vinyl, allyl, 1-butenyl, etc. When R is alkynyl, it may typically be ethynyl, propynyl, butynyl, etc. R may be inertly substituted, i.e. it may bear a non reactive substituent such as alkyl, aryl, cycloalkyl, ether, halogen, nitro, etc. Typically inertly substuted R groups may include 3-chloropropyl, 2-ethoxyethyl, carboethyoxymethyl, 4-methyl cyclohexyl, p-chlorophenyl, p-chlorobenzyl, 3-chloro-5-methylphenyl, etc. The preferred R groups may be $C_1$–$C_{20}$ alkyl, more preferably $C_8$–$C_{20}$ alkyl. R may be preferably be a $C_{14}$ alkyl group.

Preferably R is an alkyl group containing 1–40, preferably 8–20, more preferably 12–16, say about 14 carbon atoms. It is a feature of this invention that the fatty acid moiety may be derived from various commercially available fats and oils typified by those set forth in the following table:

TABLE

Coconut
Babassu
Palm kernel
Palm
Olive
Castor
Peanut
Rape
Beef Tallow
Lard (leaf)
Whale blubber
etc.

Preferred of such oils is coconut oil which typically contains residues of the following acids:

TABLE

| Component | Wt. % |
|---|---|
| Caprylic | 8.0 |
| Capric | 7.0 |
| Lauric | 48.0 |
| Myristic | 17.5 |
| Palmitic | 8.2 |
| Stearic | 2.0 |
| Oleic | 6.0 |
| Linoleic | 2.5 |

The hydroxy hydrocarbyl mercapto moiety in the ester, characterized by the formula HOR'S— may be derived from a mercapto alcohol HOR'SH.

In the above compound, R' may be a divalent hydrocarbon group selected from the group consisting of alkylene, aralkylene, cycloalkylene, arylene, alkarylene, alkenylene, and alkynylene including such radicals when inertly substituted. When R' is alkylene, it may typically be methylene, ethylene, n-propylene, iso-propylene, n-butylene, i-butylene, sec-butylene, amylene, octylene, decylene, octadecylene, etc. When R' is aralkyl, it may typically be benzylene, beta-phenylethylene, etc. When R' is cycloalkylene, it may typically be cyclohexylene,1 cycloheptylene, cyclooctylene, 2-methylcycloheptylene, 3-butylcyclohexylene, 3-methylcycloheylene, etc. When R' is arylene, it may typically be phenylene, naphthylene, etc. When R' is alkarylene, it may typically be tolylene, xylylene, etc. When R' is alkenylene, etc. When R' is alkynylene, it may typically be ethynylene, propynylene, butynylene, etc. R' may be inertly substituted, i.e. it may bear a non-reactive substituent such as alkyl, aryl, cycloalkyl, ether, halogen, nitro, etc. Typically inertly substituted R' groups may include 3-chloropropylene, 2-ethoxyethylene, carboethoxymethylene, 4-methyl cyclohexylene, p-chlorophenylene, p-chlorobenzylene, 3-chloro-5-methylphenylenel, etc. The preferred R' groups may be lower alkylene, i.e. $C_1$–$C_{10}$ alkylene, groups including, e.g. methylene, ethylene, n-propylene, i-propylene, butylene, amylene, hexylene, octylene, decylene, etc. R may preferably be —$CH_2$—$CH_2$—.

Illustrative mercaptoalcohols which may be employed in practice of this invention (as their ester with the acids supra) may be the following:

TABLE 2-mercaptoethanol
3-mercaptopropanol
1-ethyl-2-mercaptoethanol
1-ethyl-3-mercaptopropanol The reaction between the acid and the alcohol may be effected by direct reaction of the acid and the alcohol under esterification reaction conditions. In the preferred embodiment the reaction (a saponification or transesterification) may be effected by heating the oil and e.g. coconut oil (an ester) with mercapto alcohol in the presence of esterification catalyst. The amount of acid-bearing moiety (e.g. the coconut oil in the preferred embodiment) may be sufficient to yield 0.1-1 mole of acid bearing moiety per mole of thioalcohol. Although the oil may be present in amount sufficient to yield acid-bearing moieties at the lower end of the noted range (in which instance unreacted thioalcohol would be removed by distillation during the reaction), it is preferred that the oil be present in amount to yield acid-bearing moieties substantially equivalent to the thioalcohol. No advantage is observed if the coconut oil is present in excess. In the preferred embodiment, the oil is present in amounts substantially equivalent to the thioalcohol. Esterification may be effected by heating at 100° C.-160° C., say 150° C. for 2-24 hours, say 4 hours (to remove by-product water). The product may be employed as so prepared.

Typical esters which may be employed include those characterized by the formula RCO—SR'OH. Illustrative esters may include those set forth in the following Table:

TABLE $C_{10}H_{21}COSCH_2CH_2OH$
$C_{11}H_{23}COSCH_2CH_2OH$
$C_{12}H_{25}COSCH_2CH(CH_3)OH$
$C_{14}H_{29}COSCH_2CH_2CH_2OH$
$C_9H_{19}COSCH_2CH_2OH$
Coconut oil fatty acid ester of $HOCH_2CH_2SH$
Peanut oil fatty acid ester of $HOCH_2CH_2SH$
Corn oil fatty acid ester of $HOCH_2CH_2SH$ The preferred ester may be that prepared by reacting substantially equimolar quantities of coconut oil fatty acids and beta-mercaptoethanol

RCOOH+$HSCH_2CH_2OH$→$RCOSCH_2CH_2OH$ wherein R contains residues of the coconut oil acids noted supra. This may be achieved for example by reacting one mole of coconut oil with three moles of thioalcohol.

It is a feature of this invention in certain of its aspects that the desired mercaptoesters may be prepared by the reaction of a fat or fatty oil typified by those set forth in the Table supra with the mercaptoalcohol. In accordance with certain of its aspects, this invention is directed to a method which comprises reacting (i) a mercaptoalcohol and (ii) a polyester of a polyhydroxy alcohol thereby transesterifying said polyester of said polyhydroxy alcohol and forming product mercaptoester of said mercapto alcohol; and recovering said product mercapto ester of said mercapto alcohol. This transesterification may be typically as follows:

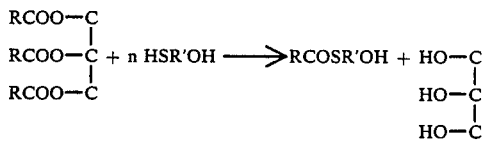

The reaction is typically carried out at 100° C. to 160° C., say 150° C. for 2-24 hours, say 4 hours in the presence of transesterification catalyst typified by calcium oxide, calcium hydroxide, toluene sulfonic acid, potassium hydroxide, methane sulfonic acid, etc. The product may be employed as prepared; and the hydroxy-containing by-product (including glycerine in the illustrative example) need not be separated.

It is a feature of this invention that these thioester additives may be added to a major portion of a hydrocarbon lubricating oil as a minor effective portion of 0.01-5 w%, preferably 0.05-5 w%, preferably 0.25-2 w%, say 0.5 w%.

The lubricating oils which may be employed in practice of the process of this invention may include a wide variety of hydrocarbon or synthetic lubricating oils used for example in automotive, aircraft, railroad, diesel, marine, tractor, etc. lubricating service—for heavy duty or light duty, for winter or summer operations, etc.

It is a feature of this invention that lubricating compositions containing effective amounts of the additive of this invention may be characterized by anti-wear and anti-friction properties. The low cost of the additives makes it possible in many instances to attain results comparable to prior art commercial friction modifiers but at lower cost. The products of this invention show exceptional anti-wear properties; in many instances, they can be used in place of the commercially used zinc dithiophosphate—and they do this in a system to which no phosphorus has been added. This is desirable because of the deleterious effect phosphorus has on catalytic converters.

The anti-wear properties of lubricating compositions containing the additives of this invention may show improved results when tested by the Four Ball Wear Test.

THE FOUR BALL WEAR TEST

The Four Ball Wear Test is carried out by securely clamping three highly polished steel balls (each 0.5 inch in diameter) in a test cup in an equilateral triangle in a horizontal plane. The fourth highly polished steel ball, resting on the three lower balls to form a tetrahedron, is held in a chuck. A weight lever arm system applies weight to the test cup, and this load holds the balls together. In the standard test, the speed of rotation is 1800 rpm; the load is 40 kilograms. The assembly is submerged in the liquid to be tested. The test is carrid out at 200° F. for 60 minutes. As the chuck and upper ball rotate against the fixed lower balls, the friction of the upper ball rotating in relation to the lower balls produces a wear-scar the diameter of which (i.e. the depth along a diameter of the ball) is measured. The average of the wear on the three lower balls is the rating assigned (in millimeters).

The anti-friction properties of the additives of this invention may be equal to the "good reference" when tested in the Small Engine Friction Test (SEFT).

SMALL ENGINE FRICTION TEST

The Small Engine Friction Test (SEFT) uses a single cylinder, air-cooled, 6-horsepower engine driven by an electric motor. The engine has a cast-iron block and is fitted with an aluminum piston and chrome-plated rings. The electric motor is cradle-mounted so that the reaction torque can be measured by a strain arm. The engine is housed in a thermally insulated enclosure with an electric heater and is driven at 2000 rpm.

Prior to each test, the engine is flushed three times with 1-quart changes of test oil. During the test run, the engine and oil temperatures are increased continually from ambient until a 280° F. oil temperature is reached. The heat comes from engine friction, air compression work and from the electric heater. The engine and oil temperatures and the engine motoring torque are recorded continually during the test. A SEFT run takes about 4 hours. Each test oil evaluation is preceded by a run on a reference oil for a like period of time. The torque reference level for the engine shifts very slowly with time as a result of engine wear. Therefore, the test oil results are recorded compared to a reference band consisting of data from up to three reference runs made before and three runs made after the test oil evaluation.

The anti-wear properties are also shown to be satisfactory when subjected to Sequence III D Test.

THE SEQUENCE III D TEST

In this test, an oil formulation is tested to evaluate the oxidative stability and wear protection of the oil. The engine is operated at high speeds (3000 rpm) for 64 hours with a high load and high operation temperature.

DESCRIPTION OF PREFERRED EMBODIMENTS

Practice of the process of this invention will be apparent to those skilled in the art from the following, wherein, as elsewhere in this specification, all parts are part by weight unless otherwise noted.

EXAMPLE I

In this example which represents the best mode known of practicing the process of this invention, the following reactants were employed:

| Reactant | grams | moles |
| --- | --- | --- |
| Beta-mercaptoethanol | 39 | 0.5 |
| Isopropanol (50 ml) | | |
| Potassium Hydroxide | 0.5 | |
| Coconut Oil | 164 | 0.25 |

The first three reactants were charged. With agitation the coconut oil was added and the reaction mixture was heated to 100° C.–140° C. under reflux for about 19 hours. The isopropyl alcohol solvent was removed by rotary evaporation. Product was recovered in amount of 201 g. Analysis showed 7.2 w%S, Sap. No. of 146, and hydroxy number of 123.9.

EXAMPLE II

The same reactants were used as in Example I except that the beta-mercaptoethanol was present in amount of 58.6 g (0.75 moles), the isopropanol was present in amount of 10 ml, and the potassium hydroxide was present in amount of 0.05 g. Product was recovered in amount of 221 g. Analysis showed 9.9%S, Sap, No. of 126.2, and hydroxy number of 264.

EXAMPLE III

In this example, the following reactants were employed:

| Reactant | grams | moles |
| --- | --- | --- |
| Corn Oil | 328 | |
| 2-mercaptoethanol | 105.5 | 1.35 |
| 70% methanesulfonic acid | 0.5 | |

The reactants were charged, nitrogen blanketed, heated to 130° C., and maintained at that temperature for 5 hours. The reaction mixture was then stripped at 100° C./20 mm.Hg., cooled to room temperature, and filtered.

EXAMPLE IV

The procedure of Example III was followed using Peanut Oil in place of Corn Oil.

EXAMPLE V

The procedures of Example III was followed using Sunflower Oil in place of Corn Oil.

EXAMPLE VI

In this example, the following reactants were employed:

| Reactants | grams | moles |
| --- | --- | --- |
| Coconut Oil | 328 | 0.5 |
| Potassium hydroxide | 0.25 | — |
| 2-mercaptoethanol | 105.3 | 1.35 |

The reactants were charged, nitrogen blanketed, heated to 150° C., and maintained at that temperature overnight (approx. 12 hours). The reaction was stripped at 100° C./20 mm. Hg., cooled to room temperature, and filtered.

The products of Examples III–VI were analyzed:

TABLE

| Example | % S (x-ray) | TAN (ASTM D-974) |
| --- | --- | --- |
| III | 9.9 | 21.6 |
| IV | 9.2 | 20.4 |
| V | 9.3 | 20.5 |
| VI | 6.9 | 30.1 |

EXAMPLE VII

In this Example, the experimental products of Examples I–II and the prior art control ZDTP zinc dithiophosphate were tested in the Four Ball Wear Test at various concentrations in SNO-20 standard oil. The results were as follows:

TABLE

| Concentration | ZDTP Control | Example I | Example II |
| --- | --- | --- | --- |
| 3.0 | 0.640 | 0.39 | |
| 2.0 | 0.510 | 0.39 | |
| 1.5 | 0.460 | 0.39 | |
| 1.0 | 0.760 | 0.60 | 0.69 |
| 0.50 | 0.640 | 0.62 | 0.67 |

TABLE-continued

| Concentration | ZDTP Control | Example I | Example II |
|---|---|---|---|
| 0.25 | 0.580 | 0.64 | |
| 0.1 | 1.372 | 0.50 | |
| 0.05 | 1.828 | 0.60 | 0.90 |
| 0.025 | 1.930 | 1.905 | 1.765 |
| 0.00 | 1.75 | | |

From the above table, it is apparent that use of the system of this invention permits attainment of anti-wear protection at lower concentration than is attained by control zinc dithiophosphate compositions. Thus the products of this invention are superior anti-wear agents, as measured by this test.

EXAMPLE VIII

In this Example, the product of Example VI was added (0.25 w%) to two fully formulated base or standard 5W-30 lubricating oils (designed "A" and "B"); and the system was then subjected to the ASTM Sequence II D, III D, and V D Tests, and the ASTM CRC L-38 Test.

TABLE

| Formulations: | Base Oil "A" | "A" Plus 0.25 W % Example VI | Base Oil "B" | "B" Plus 0.25 W % Example VI | API-SF Limit |
|---|---|---|---|---|---|
| ASTM Sequence IID | | | | | |
| Average Rust | | 8.6 | | | 8.5 Min. |
| ASTM Sequence IIID | | | | | |
| Average Sludge | 9.5 | 9.7 | 9.6 | 9.6 | 9.2 Min. |
| Average Varnish | 9.3 | 9.3 | 9.2 | 9.2 | 9.1 Min. |
| Oil Ring Clogging | 4.4 | 5.4 | 6.1 | 5.0 | 4.8 Min. |
| % Viscosity Increase 64 Hours | 27 | 129 | 539 | 409 | 375 Max. |
| Wear Maximum, Mils | 13.3 | 7.9 | 20.1 | 2.6 | 8 Max. |
| Wear Average, Mils | 0.61 | 0.31 | 6.2 | 1.9 | 4 Max. |
| ASTM Sequence V-D | | | | | |
| Average Sludge | | 9.6 | | | 9.4 Min. |
| Average Sludge | | 6.7 | | | 6.7 Min. |
| Piston Skirt Varnish | | 6.7 | | | 6.6 Min. |
| Wear Maximum Mils | | 0.7 | | | 2.5 Max. |
| Wear Average Mils | | 0.5 | | | 1.0 Max. |
| ASTM CRC L-38 | | | | | |
| Bearing Weight Loss, MG. | | 26.5 | | 23.6 | 40 Max. |

From the above table, it is apparent that the products of this invention show effective anti-wear, and maintain rust inhibition and anti-corrosion properties. The base oil without the additive failed the test.

Although this invention has been illustrated by reference to specific embodiments, it will be apparent to those skilled in the art that various changes and modifications may be made which clearly fall within the scope of this invention.

What is claimed is:

1. A lubricating composition comprising (i) a major portion of a lubricating oil; and (ii) a minor effective portion of 0.01 w%–5 w% as additive, a hydroxyhydrocarbyl mercapto ester of a saturated $C_1$–$C_{40}$ fatty acid wherein said additive comprises a beta-hydroxy-ethyl ester of a fatty acid contained in coconut oil.

2. A lubricating composition as claimed in claim 1 wherein said additive comprises a gamma-hydroxy-propyl ester of a fatty acid contained in coconut oil.

3. A lubricating composition comprising
   (i) a major portion of a hydrocarbon lubricating oil; and
   (ii) a minor effective amount of 0.1–2 w% of as additive, a beta-hydroxethyl ester of a saturated fatty acid contained in coconut oil.

4. The method which comprises adding to a major portion of a lubricating oil, a minor effective portion of, 0.01 w%–5 w% as additive, a hydroxyhydrocarby mercapto ester of a $C_1$–$C_{40}$ fatty acid wherein said additive is a beta-hydroxy-ethyl ester of a saturated fatty acid contained in coconut oil.

5. The method of claim 4 wherein said additive is a gamma-hydroxy-propyl ester of a saturated fatty acid contained in coconut oil.

6. The method which comprises adding to a major portion of a lubricating oil, a minor effective portion of 0.01–5 w%, as additive, of beta-hydroxyethyl ester of a saturated fatty acid contained in coconut oil.

7. A halogen-free hydroxyhydrocarbyl mercapto ester of a saturated $C_1$–$C_{40}$ fatty acid wherein said hydrocarbyl group is an alkyl group containing 2–3 carbon atoms.

8. A halogen-free hydroxy ethyl mercapto ester of a saturated fatty acid contained in coconut oil.

9. The method which comprises reacting (i) a mercapto alcohol and (ii) a polyester of a polyhydroxy alcohol thereby transesterifying said polyester of said polyhydroxy alcohol and forming product mercapto ester of said mercapto alcohol; and recovering said product mercapto ester of said mercapto alcohol.

10. The method of claim 9 wherein said polyester of a polyhydroxy alcohol is coconut oil.

11. Halogen-free RCOSR"OH wherein R is a saturated hydrocarbyl group containing 1–40 carbon atoms and R" is a sulfur-and-oxygen-bound alkylene group.

* * * * *